(12) United States Patent
Rolston (10) Patent No.: US 8,690,955 B2
(45) Date of Patent: Apr. 8, 2014

(54) DEVICE FOR UNICOMPARTMENTAL KNEE ARTHROPLASTY

(76) Inventor: Lindsey R. Rolston, New Castle, IN (US)

( * ) Notice: Subject to any disclaimer, the term of this patent is extended or adjusted under 35 U.S.C. 154(b) by 0 days.

(21) Appl. No.: 13/582,820

(22) PCT Filed: Mar. 9, 2011

(86) PCT No.: PCT/US2011/027739
§ 371 (c)(1),
(2), (4) Date: Sep. 5, 2012

(87) PCT Pub. No.: WO2011/112710
PCT Pub. Date: Sep. 15, 2011

(65) Prior Publication Data
US 2012/0330431 A1  Dec. 27, 2012

Related U.S. Application Data

(60) Provisional application No. 61/312,112, filed on Mar. 9, 2010.

(51) Int. Cl.
*A61F 2/38* (2006.01)
(52) U.S. Cl.
USPC ................................. 623/20.32; 623/20.34
(58) Field of Classification Search
CPC ...................................... A61F 2/389
USPC ................. 623/20.32–20.34, 20.21
See application file for complete search history.

(56) References Cited

U.S. PATENT DOCUMENTS

| | | | |
|---|---|---|---|
| 5,019,103 A * | 5/1991 | Van Zile et al. | 623/20.34 |
| 5,480,445 A * | 1/1996 | Burkinshaw | 623/20.32 |
| 5,549,683 A | 8/1996 | Bonutti | |
| 2003/0100953 A1 * | 5/2003 | Rosa et al. | 623/20.3 |
| 2004/0006393 A1 * | 1/2004 | Burkinshaw | 623/20.3 |
| 2005/0143831 A1 | 6/2005 | Justin et al. | |
| 2006/0116743 A1 | 6/2006 | Gibson et al. | |
| 2006/0235517 A1 * | 10/2006 | Hodorek | 623/14.12 |
| 2007/0032876 A1 | 2/2007 | Clark | |
| 2008/0027557 A1 * | 1/2008 | Tuke | 623/20.32 |
| 2008/0133020 A1 * | 6/2008 | Blackwell et al. | 623/20.34 |
| 2009/0084491 A1 | 4/2009 | Uthgenannt et al. | |

OTHER PUBLICATIONS

International Searching Authority, Written Opinion of the International Searching Authority, mailed Sep. 11, 2012 (PCT/US2011/027739).
International Searching Authority, International Search Report, mailed Sep. 11, 2012 (PCT/US2011/027739).

* cited by examiner

*Primary Examiner* — Jason-Dennis Stewart
(74) *Attorney, Agent, or Firm* — Ice Miller LLP (57) ABSTRACT

A device for unicompartmental arthroplasty of the knee. The device permits arthroplasty of the medial and/or lateral tibial condyle, and allows for securing of the device without the use of bone cement. Such a device comprises a baseplate, the baseplate comprising a first surface configured to be secured to a surgically prepared medial (or lateral) compartment of a proximal end of a patient's tibia, and an opposing second surface configured to replicate a medial (or lateral) tibial condyle; a flange adjacent the baseplate, the flange shaped to interface with a surgically prepared anterior surface of the proximal end of the patient's tibia, the flange comprising an orifice therethrough; and at least one anchor protruding from the first surface, the at least one anchor arranged to coincide with at least one corresponding surgically prepared void in the patient's tibia.

32 Claims, 9 Drawing Sheets

FIG. 8

# DEVICE FOR UNICOMPARTMENTAL KNEE ARTHROPLASTY

RELATED APPLICATIONS

The present application is related to, claims the priority benefit of and is a U.S. §371 national stage entry of , International Patent Application Serial No. PCT/US2011/027739, filed Mar. 9, 2011, which is related to and claims the priority benefit of U.S. Provisional Patent Application Ser. No. 61/312,112, filed Mar. 9, 2010. The contents of each of these applications are hereby incorporated by reference in their entirety into this disclosure.

BACKGROUND OF THE INVENTION

Arthritic damage to portions of the knee joint can severely limit an individual's ability to walk or enjoy recreational activities. The extent of arthritic damage may be far reaching, affecting all compartments of the knee joint, or the damage may be limited to a single compartment of the knee ("unicompartmental osteoarthritis"), requiring only resurfacing or replacement of a single surface rather than total knee replacement surgery. In understanding unicompartmental joint reconstruction, practitioners typically refer to three separate areas of joint articulation as if they were separate compartments: the inner part of the joint between femur and tibia (the "medial compartment"), the outer part of the joint between femur and tibia (the "lateral compartment") and the joint between the patella and the femur (the "patello-femoral compartment"). If osteoarthritis affects a patient only in the lateral or medial compartment of the knee, unicondylar knee arthroplasty often is a preferred method of treatment, as the surgery is far less invasive, and allows for more rapid recovery while maintaining the integrity of unaffected areas of the knee, often allowing the anterior and posterior cruciate ligaments to remain intact.

As such, unicondylar knee arthroplasty has gained popularity in the recent years for treating medial compartment osteoarthritis of the knee joint, and has proven to be a successful surgery for people with this degenerative arthritis of the knee. The inside (medial) component (medial tibial plateau and the medial femoral condyle) is most commonly involved and replaced using unicompartmental arthroplasty. However, occasionally, the outside (lateral) compartment (the lateral tibial plateau and the lateral femoral condyle) is involved and must be replaced.

While a unicondylar arthroplasty is far less invasive on the patient, it should be appreciated that when only a single condyle of the tibia is resurfaced and replaced with an implant, there is less surface area to attach an implant and receive anchors to secure the implant that will receive stresses in nearly all directions almost immediately after the surgery is performed. Traditionally, bone cement was used to secure such an implant into place, thereby securing the implant and filling any voids between the contoured condyle and the bottom surface of the implant. However, bone cement can weaken and crack over time, causing failure of the implant, and/or creating debris within the knee compartment. The flexing motion of the knee is known to cause an implant on the tibial plateau to lift off anteriorly, which also may cause failure of the implant and/or produce debris within the knee compartment. Further, any excess cement that is not cleared from the compartment during surgery can cause inflammation or result in debris within the compartment.

Efforts to improve long term success of tibial implants and reduce the inflammation or failure that can be caused by the use of bone cement include the use of highly porous metal or Trabecular Metal implants to encourage better bone growth into the implant for long term retention of the implant, but securing such an implant through the ingrowth of the patient's cancellous bone requires a significant amount of time, and proper integration requires that the implant be securely held in place while the integration occurs. Considering the significant forces associated with weight bearing and activity as distributed over the small surface area of the tibia, there is concern that porous implants may not be retained in place during the ingrowth of cancellous bone required to maintain the implant during the healing phase. For example, the flexing motion of the knee is known to cause a tibial baseplate to lift off anteriorly, hindering bone ingrowth in a porous metal implant. As such, an implant having an ability to be secured to the anterior medial condyle of a tibia without the use of bone cement would be advantageous.

SUMMARY

The present disclosure includes disclosure of a device for unicompartmental arthroplasty of a patient's knee.

In at least one embodiment, such a device comprises a baseplate, the baseplate comprising a first surface configured to be secured to a surgically prepared medial (or lateral) compartment of a proximal end of a patient's tibia, and an opposing second surface configured to replicate a medial (or lateral) tibial condyle; a flange adjacent the baseplate, the flange shaped to interface with a surgically prepared anterior surface of the proximal end of the patient's tibia, the flange comprising an orifice therethrough; and at least one anchor protruding from the first surface, the at least one anchor arranged to coincide with at least one corresponding surgically prepared void in the patient's tibia.

In at least one embodiment, a device for unicompartmental arthroplasty of a patient's knee comprises a baseplate, the baseplate comprising a first surface configured to be secured to a surgically prepared medial (or lateral) compartment of a proximal end of a patient's tibia, an opposing second surface configured to replicate a medial (or lateral) tibial condyle, and an anterior slot; at least one anchor protruding from the first surface, the at least one anchor arranged to coincide with at least one corresponding surgically prepared void in the patient's tibia; and a flange, the flange shaped to be secured to a surgically prepared anterior surface of the proximal end of the patient's tibia, the flange comprising an orifice therethrough and a tab protruding therefrom, wherein when the baseplate is secured to the surgically prepared medial (or lateral) compartment of the proximal end of the patient's tibia, and the flange is secured to the surgically prepared anterior surface of the proximal end of the patient's tibia, the tab is inserted into the slot.

In an aspect of a device for unicompartmental arthroplasty of a patient's knee according to the present disclosure, such a device comprises a receptacle in at least one anchor, and a rod-like fastener comprising a first end, where the fastener is installed through the orifice, and the first end of the fastener is received in the receptacle. In an aspect of a device for unicompartmental arthroplasty of a patient's knee according to the present disclosure, such a device comprises internal threads in the receptacle, and external threads on the first end of the fastener, where the external threads are complementary to the internal threads in the receptacle.

In an aspect of a device for unicompartmental arthroplasty of a patient's knee according to the present disclosure, such a device comprises internal threads in the orifice, a rod-like fastener comprising a first end and a second end, where the fastener installed through the orifice and the second end of the fastener is received in the orifice, and external threads on the second end of the fastener that are complementary to the internal threads in the orifice.

In an aspect of a device for unicompartmental arthroplasty of a patient's knee according to the present disclosure, such a device comprises a receptacle in the first surface, and a rod-like fastener comprising a first end, the fastener installed through the orifice, and the first end of the fastener received in the receptacle. In an aspect of a device for unicompartmental arthroplasty of a patient's knee according to the present disclosure, such a device comprises internal threads in the receptacle; and external threads on the first end of the fastener, the external threads being complementary to the internal threads in the receptacle.

The present disclosure includes disclosure of methods of performing unicompartmental arthroplasty of a patient's knee. In at least one embodiment, the method comprises the steps of making an incision along an anterior medial (or lateral) aspect of the knee; excising any remnants of the medial (or lateral) meniscus; surgically preparing a medial (or lateral) compartment of the patient's tibia to receive a medial (or lateral) tibial prosthesis component in a manner so as to preserve the integrity of a anterior and posterior cruciate ligaments, the medial (or lateral) tibial prosthesis component having a baseplate, the baseplate comprising a first surface configured to be secured to a surgically prepared medial (or lateral) compartment of a proximal end of a patient's tibia, and an opposing second surface configured to replicate a medial (or lateral) tibial condyle, a flange adjacent the baseplate, the flange shaped to interface with a surgically prepared anterior surface of the proximal end of the patient's tibia, the flange comprising an orifice therethrough, and at least one anchor protruding from the first surface, the at least one anchor arranged to coincide with at least one corresponding surgically prepared void in the patient's tibia; securing the medial (or lateral) tibial prosthesis component to the tibia; and closing the incision.

BRIEF DESCRIPTION OF THE DRAWINGS

The features and advantages of this disclosure, and the manner of attaining them, will be more apparent and better understood by reference to the following descriptions of the disclosed methods and systems, taken in conjunction with the accompanying drawings, wherein.

DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure includes disclosure of a device for unicompartmental arthroplasty of a patient's knee. In at least one embodiment, such a device comprises a baseplate and an anterior flange, with a fastening structure interacting with the anterior flange to deter anterior lift off of the tibial baseplate.

Figure 1:
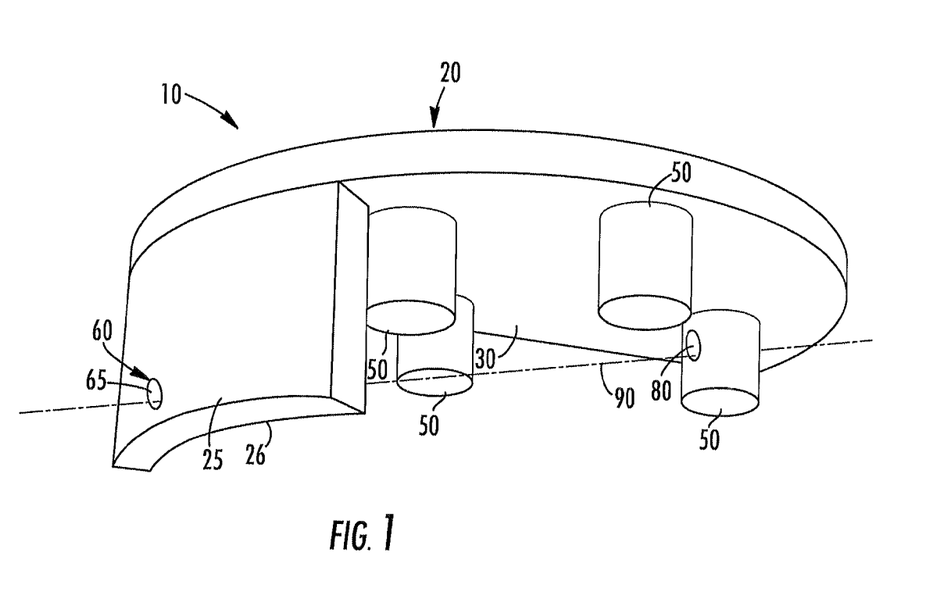
FIG. 1 shows a perspective view of a tibial prosthesis component in accordance with at least one embodiment of the present disclosure.
Figure 2:
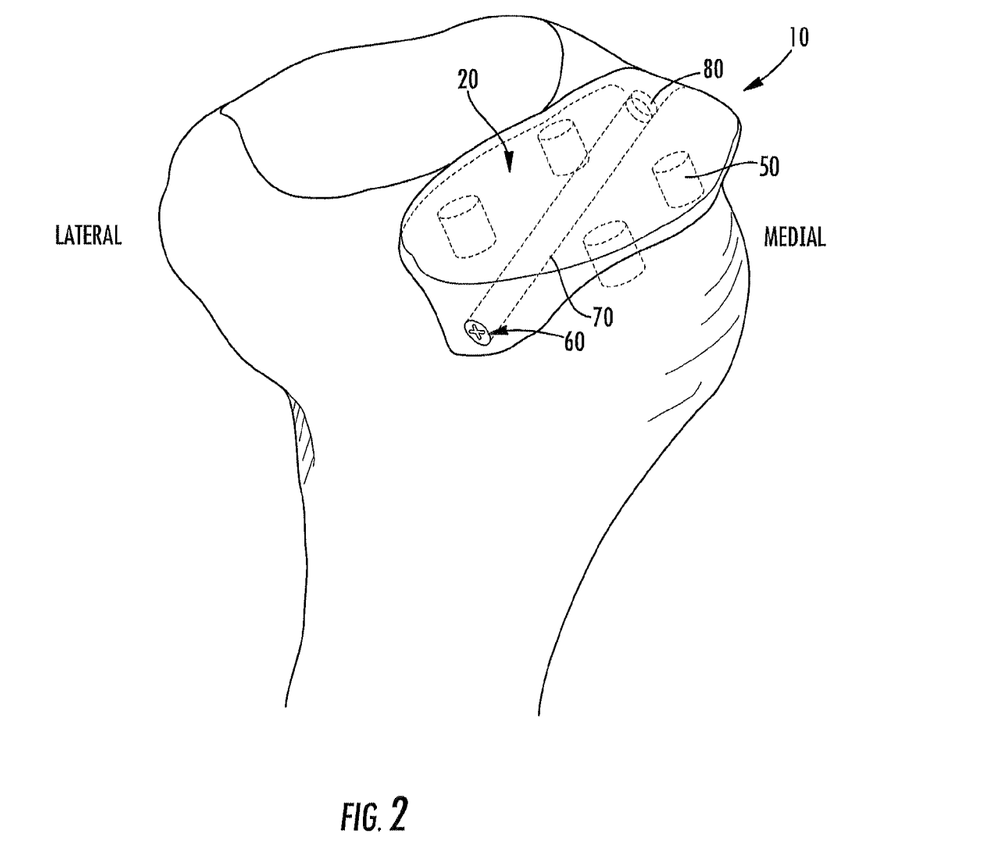
FIG. 2 shows an anterior medial perspective view of a tibial prosthesis component in accordance with at least one embodiment of the present disclosure, as placed upon a patient's tibia.
Figure 3:
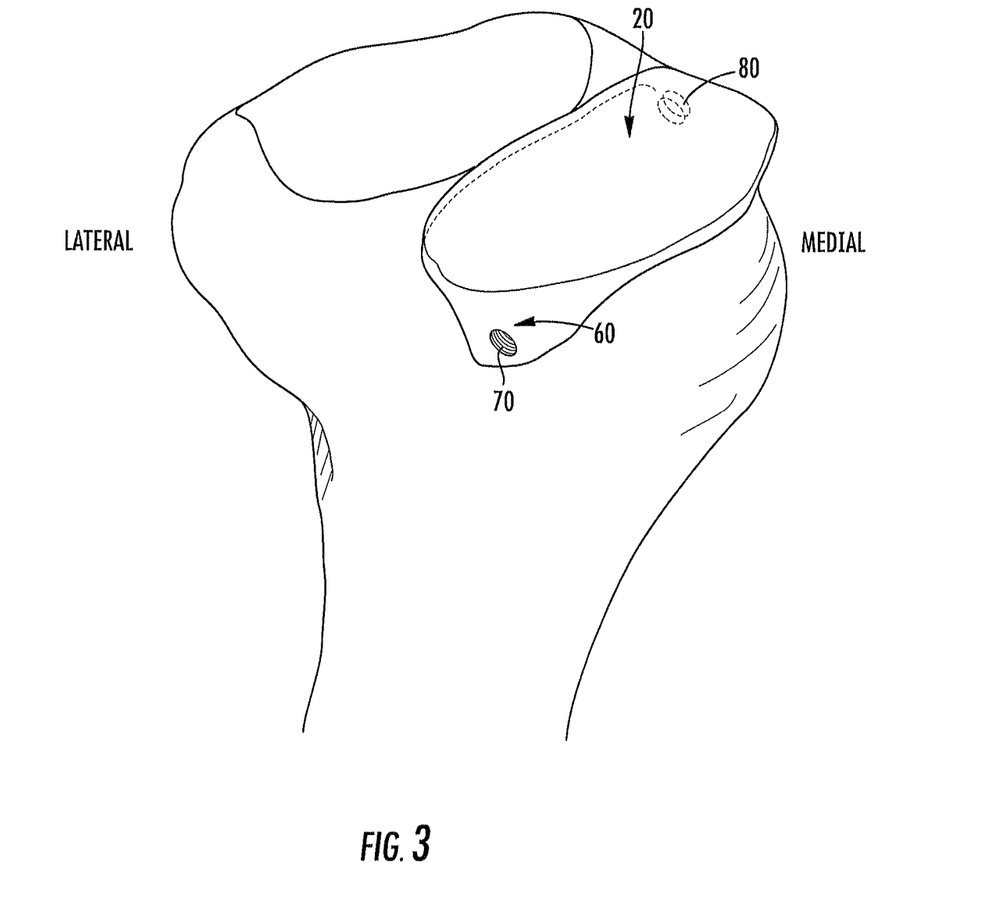
FIG. 3 shows an anterior medial perspective view of a tibial prosthesis component in accordance with at least one embodiment of the present disclosure, as surgically implanted upon and secured to a patient's tibia.

FIG. 1 shows a medial tibial prosthesis component 10 according to at least one embodiment of the present disclosure, for use in connection with a medial tibial condyle resurfacing. Prosthesis 10 comprises a baseplate having an upper surface 20 for interfacing with the corresponding femoral condyle and lower surface 30 for interfacing with a surgically prepared portion of the medial condyle of a tibia 100, as shown in FIGS. 2-3 and described in more detail below. In at least one embodiment of the present disclosure, prosthesis 10 comprises anterior flange 25 for interfacing with a surgically prepared anterior portion of the medial condyle of tibia 100.

As shown in FIG. 1, lower surface 30 comprises a least one anchor 50 protruding therefrom. In at least one embodiment of the present disclosure, such anchors 50 protrude between about 7-9 mm from lower surface 30. According to at least one embodiment of the present disclosure, anchors 50 interface with cancellous bone of the tibia. In such an embodiment, anchors 50 are sized and shaped to correspond to surgically created voids in the tibia. Anchors 50 are inserted into such surgically created voids in the tibia (as shown in FIG. 2), while the surgically prepared surface of the tibia interfaces with lower surface 30 and posterior surface 26 of anterior flange 25. Different embodiments of anchors 50 may have different cross-sectional shapes. In at least one embodiment, anchors 50 have a circular cross-section. In at least one embodiment, the cross-section has varying dimensions along the length of at least one anchor 50. In at least one embodiment of prosthesis 10, a plurality of anchors 50 having more than one cross-sectional shape are used.

Prosthesis 10 may comprise titanium or titanium alloys, tantalum or tantalum alloys (including those materials described as "Trabecular Metal" from Zimmer Inc., Warsaw, Ind.), porous metal, stainless steel, cobalt chrome steel, Zirconia, ceramic material, high-density polymer (such as polyetheretherketone "PEEK" or similar materials), or a combination of any of the foregoing. In at least one embodiment of the present disclosure, prosthesis 10, including anterior flange 25 and anchors 50, is constructed substantially of porous metal such as, for example, Trabecular Metal. In at least one embodiment, at least a portion of posterior surface 26 of anterior flange 25, lower surface 30, and the exterior of anchors 50 is constructed of an absorbable material. In at least one embodiment of the present disclosure, prosthesis 10, including anterior flange 25 and anchors 50, is of monolithic construction. In at least one embodiment of the present disclosure, posterior surface 26 of anterior flange 25, lower surface 30, and the exterior of anchors 50 have a rough surface for interfacing with tibial bone, or are coated with a material conducive to improving ingrowth of cancellous bone. In at least one embodiment of the present disclosure, anterior flange 25 comprise a malleable material, permitting anterior flange 25 to be conformed to the contours of the tibial condyle.

Figure 4:
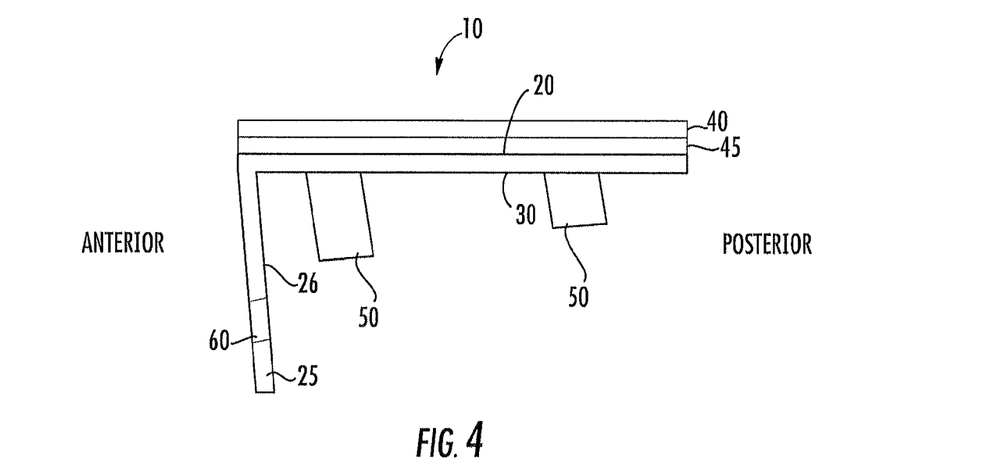
FIG. 4 shows a side view of a tibial prosthesis component in accordance with at least one embodiment of the present disclosure.

FIG. 4 shows a side view of prosthesis 10 according to at least one embodiment of the present disclosure. Shown in FIG. 4 are prosthesis 10 comprising upper surface 20, flange 25, lower surface 30, and anchors 50. The embodiment of the present disclosure shown in FIG. 4 also comprises optional intermediate layer 40 and optional polymer layer 45. As shown in FIG. 4, in at least one embodiment of the present disclosure, flange 25 and anchors 50 are not perpendicular to lower surface 30. Instead, in such an embodiment flange 25 and anchors 50 are angled toward the posterior of the prosthesis 10. Such a structure aids in installation of the prosthesis 10.

In at least one embodiment of the present disclosure, upper surface 20 of prosthesis 10 comprises a high-density polymer portion 45 that is attached to an intermediate portion 40 through adhesives, fasteners, wedged joints, or other attachment mechanisms. FIG. 4 shows an example of such an embodiment, with proportions enhanced for purposes of clarity.

In at least one embodiment of the present disclosure, flange 25 of prosthesis 10 includes at least one orifice 60, operable to allow the introduction of a fastening structure 70 through flange 25 of prosthesis 10 and through the patient's tibia. In at least one embodiment of the present disclosure, flange 25 of prosthesis 10 comprises more than one orifice 60.

In at least one embodiment of the present disclosure, fastening structure 70 may comprise a rod comprising titanium or titanium alloys, tantalum or tantalum alloys (including those materials described as "Trabecular Metal" from Zimmer Inc., Warsaw, Ind.), porous metal, ceramic material, high-density polymer, or a combination thereof, and may be solid and smooth, surfaced to have a rough exterior for interfacing with cancellous bone, coated with a material conducive to improving ingrowth of cancellous bone, or fused, bonded, or otherwise attached to the underlying material. In at least one embodiment, fastening structure 70 is constructed of an absorbable material.

In at least one embodiment of the present disclosure, fastening structure 70 may comprise a threaded rod sized and shaped to pass through orifice 60. In at least one embodiment of the present disclosure, fastening structure 70 is threaded at least at its proximal end. In such an embodiment, orifice 60 is tapped with complementary receiving threads to allow fastening structure 70 to be securely fastened within orifice 60 by the interaction of such threads.

According to at least one embodiment of the present disclosure, receptacle 80 is a portion of prosthesis 10 sized and shaped to accept a distal portion 75 of fastening structure 70. By way of nonlimiting example, distal portion 75 of fastening structure 70 may be a threaded rod having a size and thread complementary to that of receptacle 80. In such an embodiment, fastening structure 70 may be threaded along its entire length, or threaded only at its proximal and/or distal ends. In at least one exemplary embodiment, receptacle 80 of prosthesis 10 may be located toward the posterior of prosthesis 10, as shown in FIGS. 1 and 2.

In at least one embodiment of the present disclosure, a receiving structure 80 is formed in an anchor 50. In at least one embodiment of the present disclosure, receiving structure 80 is formed in lower surface 30 of prosthesis 10. Regardless of the location and structure of receptacle 80, it will be appreciated that the positioning of receptacle 80 with respect to orifice 60 will be such that the interior lumens defined by the respective structures are in line with one another. Optionally, fastening structure 70 may be secured into the patient's tibia, such as, for example, by threads or other securing methods, in addition to or in lieu of securing fastening structure 70 in orifice 60 and/or receptacle 80.

According to the exemplary embodiment of the present disclosure shown in FIG. 1, orifice 60 contains a guide receiving portion 65 that is sized and positioned to accept a surgical drill bit. Guide receiving portion 65 comprises a hollow tubular body sized and shaped to fit within orifice 60. In operation, guide receiving portion 65 is sized and shaped to accept a surgical drill bit, and guide it through orifice 60 to allow a surgeon to create a void by surgically drilling a hole through the patient's tibia at a predetermined angle that will allow fastening structure 70 to pass from orifice 60, through the patient's tibia, and into receptacle 80. It will be appreciated that guide receiving portion 65 may be threaded, or may be a friction fit that allows a surgical drill bit to be removably inserted into guide receiving portion 65 such that surgical drill bit may be removed after use, thereby allowing fastening structure 70 to be inserted through orifice 60, through the void created in the tibia by the surgical drill, and received in receptacle 80. Line 90 of FIG. 1 illustrates the path followed by fastening structure 70.

According to at least one embodiment of the present disclosure, prosthesis 10 comprises more than one fastening structure 70, along with a corresponding more than one orifice 60 and more than one receptacle 80.

FIGS. 5A-7 show a medial tibial prosthesis component 110 according to at least one embodiment of the present disclosure, for use in connection with a medial tibial condyle resurfacing. Prosthesis 110 comprises a baseplate having upper surface 120 for interfacing with the corresponding femoral condyle and lower surface 130 for interfacing with a surgically prepared portion of the medial condyle of a tibia 100.

In at least one embodiment of the present disclosure, prosthesis 110 comprises anterior flange 125 for interfacing with a surgically prepared anterior portion of the medial condyle of tibia 100. According to such an embodiment, flange 125 comprises posterior surface 126 and tab 127. According to such an embodiment, prosthesis 110 comprises anterior slot 122. According to such an embodiment, when prosthesis 110 is surgically implanted tab 127 is inserted into anterior slot 122 in the direction shown by arrow 129 in FIGS. 5A and 6.

Figure 5A:
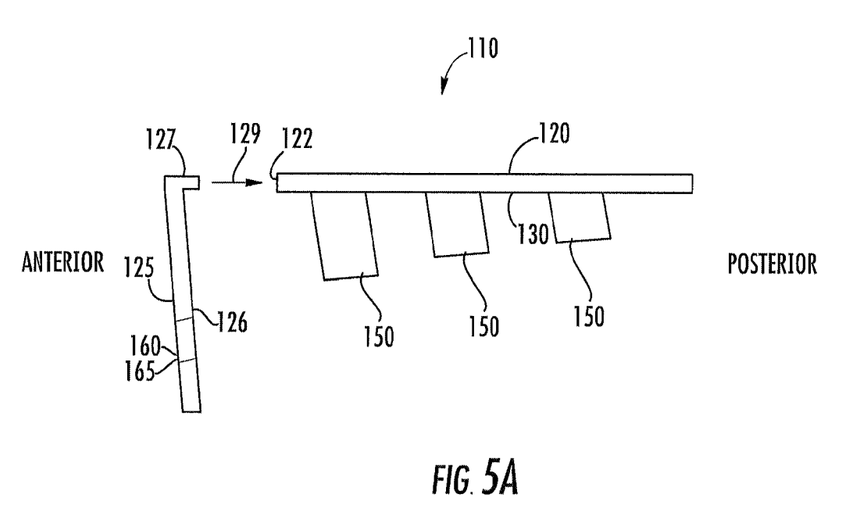
FIG. 5A shows a side view of a tibial prosthesis component in accordance with at least one embodiment of the present disclosure.
Figure 5B:
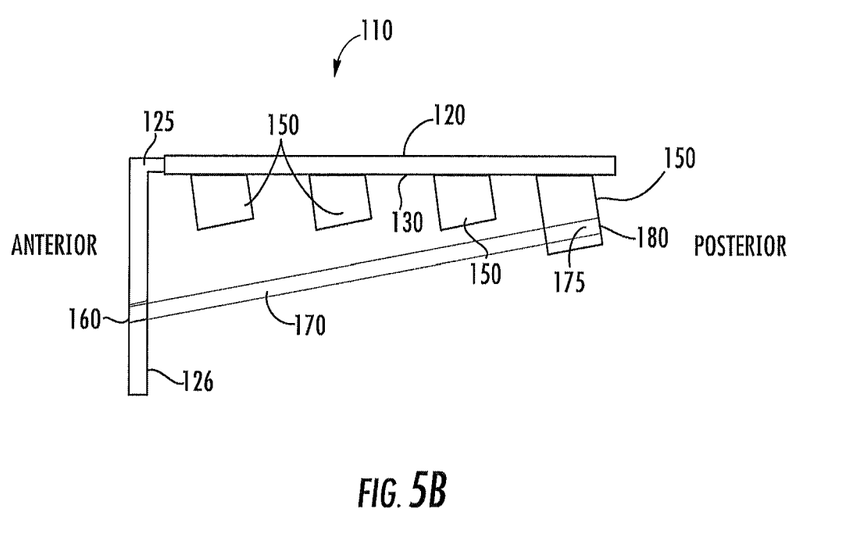
FIG. 5B shows a side view of a tibial prosthesis component in accordance with at least one embodiment of the present disclosure.
Figure 6:
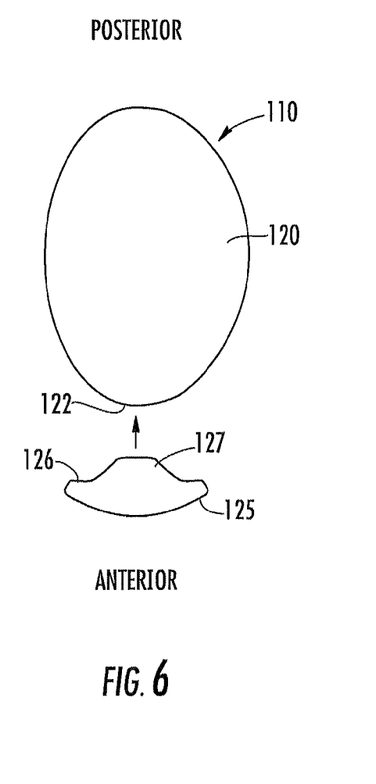
FIG. 6 shows a top view of a tibial prosthesis component in accordance with at least one embodiment of the present disclosure.
Figure 7:
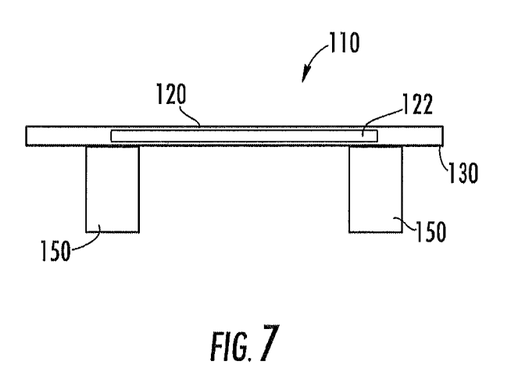
FIG. 7 shows a front elevation view of a tibial prosthesis component in accordance with at least one embodiment of the present disclosure.

As shown in FIGS. 5A-B, lower surface 130 comprises at least one anchor 150 protruding therefrom. In at least one embodiment of the present disclosure, anchors 150 protrude between about 7-9 mm from lower surface 130. According to at least one embodiment of the present disclosure, anchors 150 interface with cancellous bone of the tibia. In such an embodiment, anchors 150 are sized and shaped to correspond to surgically created voids in the tibia. Anchors 150 are inserted into such surgically created voids in the tibia, while the surgically prepared surface of the tibia interfaces with lower surface 130 and posterior surface 126 of anterior flange 125. Different embodiments of anchors 150 may have different cross-sectional shapes. In at least one embodiment, anchors 150 have a circular cross-section. In at least one embodiment, the cross-section has varying dimensions along the length of at least one anchor 150. In at least one embodiment of prosthesis 110, a plurality of anchors 150 having more than one cross-sectional shape are used.

Prosthesis 110 may comprise titanium or titanium alloys, tantalum or tantalum alloys (including those materials described as "Trabecular Metal" from Zimmer Inc., Warsaw, Ind.), porous metal, stainless steel, cobalt chrome steel, Zirconia, ceramic material, high-density polymer (such as polyetheretherketone "PEEK" or similar materials), or a combination of any of the foregoing. In at least one embodiment of the present disclosure, prosthesis 110, including anterior flange 125 and anchors 150, is constructed substantially of porous metal such as, for example, Trabecular Metal. In at least one embodiment, at least a portion of posterior surface 126 of anterior flange 125, lower surface 130, and the exterior of anchors 150 is constructed of an absorbable material. In at least one embodiment of the present disclosure, posterior surface 126 of anterior flange 125, lower surface 130, and the exterior of anchors 150 have a rough surface for interfacing with tibial bone, or are coated with a material conducive to improving ingrowth of cancellous bone. In at least one embodiment of the present disclosure, anterior flange 125 comprise a malleable material, permitting anterior flange 125 to be conformed to the contours of the tibial condyle.

FIGS. 5A-B shows a side view of prosthesis 110 according to at least one embodiment of the present disclosure. Shown in FIGS. 5A-B are prosthesis 110 comprising upper surface 120, flange 125, lower surface 130, and anchors 150. As shown in FIG. 5A, in at least one embodiment of the present disclosure, flange 125 and anchors 150 are not perpendicular to lower surface 130. Instead, in such an embodiment flange 125 and anchors 150 are angle toward the posterior of the prosthesis 110. Such a structure aids in installation of the prosthesis 110.

In at least one embodiment of the present disclosure, flange 125 of prosthesis 110 includes at least one orifice 160, operable to allow the introduction of a fastening structure 170 through flange 125 of prosthesis 110 and through the patient's tibia. In at least one embodiment of the present disclosure, flange 125 of prosthesis 110 comprises more than one orifice 160.

FIG. 5B shows such an embodiment, with the patient's tibia cutaway for purposes of clarity. In at least one embodiment of the present disclosure, upper surface 120 of prosthesis 110 comprises a high-density polymer portion that is attached to an intermediate portion through adhesives, fasteners, wedged joints, or other attachment mechanisms.

In at least one embodiment of the present disclosure, fastening structure 170 may comprise a rod comprising titanium or titanium alloys, tantalum or tantalum alloys (including those materials described as "Trabecular Metal" from Zimmer Inc., Warsaw, Ind.), porous metal, ceramic material, high-density polymer, or a combination thereof, and may be solid and smooth, surfaced to have a rough exterior for interfacing with cancellous bone, coated with a material conducive to improving ingrowth of cancellous bone, or fused, bonded, or otherwise attached to the underlying material. In at least one embodiment, fastening structure 170 is constructed of an absorbable material.

In at least one embodiment of the present disclosure, fastening structure 170 may comprise a threaded rod sized and shaped to pass through orifice 160. In at least one embodiment of the present disclosure, fastening structure 170 is threaded at least at its proximal end. In such an embodiment, orifice 160 is tapped with complementary receiving threads to allow fastening structure 170 to be securely fastened within orifice 160 by the interaction of such threads.

According to at least one embodiment of the present disclosure, receptacle 180 is a portion of prosthesis 110 sized and shaped to accept a distal portion 175 of fastening structure 170. By way of nonlimiting example, distal portion 175 of fastening structure 170 may be a threaded rod having a size and thread complementary to that of receptacle 180. In such an embodiment, fastening structure 170 may be threaded along its entire length, or threaded only at its proximal and/or distal ends. In at least one exemplary embodiment, receptacle 180 of prosthesis 110 may be located toward the posterior of prosthesis 110, as shown in FIG. 5B.

In at least one embodiment of the present disclosure, receiving structure 180 is formed in an anchor 150. In at least one embodiment of the present disclosure, receiving structure 180 is formed in lower surface 130 of prosthesis 110. Regardless of the location and structure of receptacle 180, it will be appreciated that the positioning of receptacle 180 with respect to orifice 160 will be such that the interior lumens defined by the respective structures are in line with one another. Optionally, fastening structure 170 may be secured into the patient's tibia, such as, for example, by threads or other securing methods, in addition to or in lieu of securing fastening structure 170 in orifice 160 and/or receptacle 180.

According to the exemplary embodiment of the present disclosure shown in FIGS. 5A-B, orifice 160 contains a guide receiving portion 165 that is sized and positioned to accept a surgical drill bit. Guide receiving portion 165 comprises a hollow tubular body sized and shaped to fit within orifice 160. In operation, guide receiving portion 165 is sized and shaped to accept a surgical drill bit, and guide it through orifice 160 to allow a surgeon to create a void by surgically drilling a hole through the patient's tibia at a predetermined angle that will allow fastening structure 170 to pass from orifice 160, through the patient's tibia, and into receptacle 180. It will be appreciated that guide receiving portion 165 may be threaded, or may be a friction fit that allows a surgical drill bit to be removably inserted into guide receiving portion 165 such that surgical drill bit may be removed after use, thereby allowing fastening structure 170 to be inserted through orifice, through the void created in the tibia by the surgical drill, and received in receptacle 180.

According to at least one embodiment of the present disclosure, prosthesis 110 comprises more than one fastening structure 170, along with a corresponding more than one orifice 160 and more than one receptacle 180.

Figure 8:
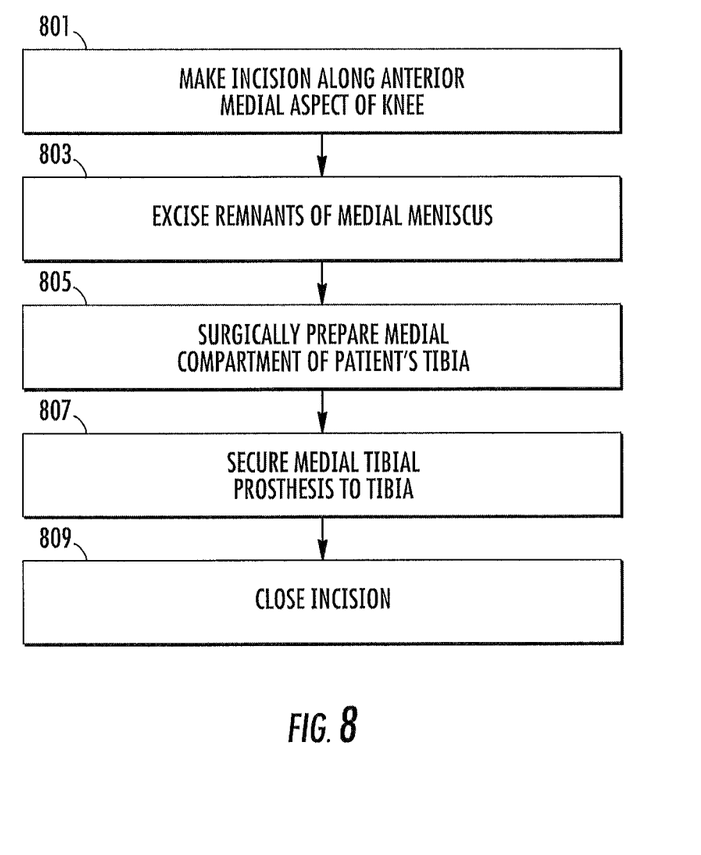
FIG. 8 shows a flow chart illustrating a method for surgically implanting a tibial prosthesis component in accordance with at least one embodiment of the present disclosure.

FIG. 8 shows a flow chart illustrating the method for implanting a prosthesis 110 according to at least one embodiment of the present disclosure. In step 801 of FIG. 8, an incision is made along an anterior medial aspect of a patient's knee. In step 803 of FIG. 8, any remnants of the medial meniscus are excised. In step 805 of FIG. 8, a medial compartment of the patient's tibia is surgically prepared to receive a medial tibial prosthesis component according to present disclosure, with such surgical preparation performed in a manner so as to preserve the integrity of the patient's anterior and posterior cruciate ligaments. In step 805 of FIG. 8, the medial tibial prosthesis component according to present disclosure is secured to the patient's tibia. In step 807 of FIG. 8, the incision is closed.

While this disclosure has been described as having a preferred design, the systems and methods according to the present disclosure can be further modified within the scope and spirit of this disclosure. This application is therefore intended to cover any variations, uses, or adaptations of the disclosure using its general principles. For example, although the disclosure herein has discussed unicompartmental arthroplasty for the medial compartment of a patient's knee, the devices and methods disclosed herein may be readily adapted for the lateral compartment of a patient's knee, and such adaptations are within the scope of the present disclosure. In addition, the methods disclosed herein and in the appended claims represent one possible sequence of performing the steps thereof. A practitioner may determine in a particular implementation that a plurality of steps of one or more of the disclosed methods may be combinable, or that a different sequence of steps may be employed to accomplish the same results. Each such implementation falls within the scope of the present disclosure as disclosed herein and in the appended claims. Furthermore, this application is intended to cover such departures from the present disclosure as come within known or customary practice in the art to which this disclosure pertains and which fall within the limits of the appended claims.

What is claimed is:

1. A device for unicompartmental arthroplasty of a knee comprising:
a baseplate, said baseplate comprising a first surface configured to be secured to a surgically prepared proximal end of a patient's tibia, and an opposing second surface configured to replicate a tibial condyle;
a flange adjacent said baseplate, said flange shaped to interface with a surgically prepared anterior surface of said proximal end of said patient's tibia, said flange comprising an orifice therethrough;
at least one anchor protruding from said first surface, said at least one anchor arranged to coincide with at least one corresponding surgically prepared void in said patient's tibia;
a receptacle in at least one said anchor; and
a rod-like fastener comprising a first end, said fastener installed through said orifice, said first end of said fastener received in said receptacle.

2. The device for unicompartmental arthroplasty of claim 1, wherein said baseplate comprises a porous metal material.

3. The device for unicompartmental arthroplasty of claim 1, wherein said flange comprises a porous metal material.

4. The device for unicompartmental arthroplasty of claim 1, wherein said at least one anchor comprises a porous metal material.

5. The device for unicompartmental arthroplasty of claim 1, wherein said baseplate is configured to be secured to said patient's tibia without using cement.

6. The device for unicompartmental arthroplasty of claim 1, further comprising:
internal threads in said receptacle; and
external threads on said first end of said fastener, said external threads being complementary to said internal threads in said receptacle.

7. The device for unicompartmental arthroplasty of claim 1, further comprising:
internal threads in said orifice; and
external threads on said fastener, said external threads being complementary to said internal threads in said orifice.

8. A device for unicompartmental arthroplasty of a knee comprising:
a baseplate, said baseplate comprising a first surface configured to be secured to a surgically prepared proximal end of a patient's tibia, and an opposing second surface configured to replicate a tibial condyle;
a flange adjacent said baseplate, said flange shaped to interface with a surgically re ared anterior surface of said eroximal end of said patient's tibia, said flange comprising an orifice therethrough;
a receptacle in said first surface; and
a rod-like fastener comprising a first end, said fastener installed through said orifice, said first end of said fastener received in said receptacle.

9. The device for unicompartmental arthroplasty of claim 8, further comprising:
internal threads in said receptacle; and
external threads on said first end of said fastener, said external threads being complementary to said internal threads in said receptacle.

10. The device for unicompartmental arthroplasty of claim 8, further comprising:
at least one anchor protruding from said first surface, said at least one anchor arranged to coincide with at least one corresponding surgically prepared void in said patient's tibia.

11. The device for unicompartmental arthroplasty of claim 10, wherein said at least one anchor comprises a porous metal material.

12. The device for unicompartmental arthroplasty of claim 8, wherein said baseplate comprises a porous metal material.

13. The device for unicompartmental arthroplasty of claim 8, wherein said flange comprises a porous metal material.

14. The device for unicompartmental arthroplasty of claim 8, wherein said baseplate is configured to be secured to said patient's tibia without using cement.

15. The device for unicompartmental arthroplasty of claim 8, further comprising:
internal threads in said orifice; and
external threads on said fastener, said external threads being complementary to said internal threads in said orifice.

16. A device for unicompartmental arthroplasty of a knee comprising:
a baseplate, said baseplate comprising a first surface configured to be secured to a surgically prepared proximal end of a patient's tibia, an opposing second surface configured to replicate a tibial condyle, and an anterior slot;
at least one anchor protruding from said first surface, said at least one anchor arranged to coincide with at least one corresponding surgically prepared void in said patient's tibia;
a flange, said flange shaped to be secured to a surgically prepared anterior surface of said proximal end of said patient's tibia, said flange comprising an orifice therethrough and a tab protruding therefrom, wherein when said baseplate is secured to said surgically prepared proximal end of said patient's tibia, and said flange is secured to said surgically prepared anterior surface of said proximal end of said patient's tibia, said tab is inserted into said slot;
a receptacle in at least one said anchor; and
a rod-like fastener comprising a first end, said fastener installed through said orifice, said first end of said fastener received in said receptacle.

17. The device for unicompartmental arthroplasty of claim 16, wherein said baseplate comprises a porous metal material.

18. The device for unicompartmental arthroplasty of claim 16, wherein said flange comprises a porous metal material.

19. The device for unicompartmental arthroplasty of claim 16, wherein said at least one anchor comprises a porous metal material.

20. The device for unicompartmental arthroplasty of claim 16, wherein said baseplate is configured to be secured to said patient's tibia without using cement.

21. The device for unicompartmental arthroplasty of claim 16, further comprising:

internal threads in said receptacle; and
external threads on said first end of said fastener, said external threads being complementary to said internal threads in said receptacle.

22. The device for unicompartmental arthroplasty of claim 16, further comprising:
internal threads in said orifice; and
external threads on said fastener, said external threads being complementary to said internal threads in said orifice.

23. A device for unicompartmental arthroplasty of a knee comprising:
a baseplate, said baseplate comprising a first surface configured to be secured to a surgically prepared proximal end of a patient's tibia, an opposing second surface configured to re slicate a tibial cond le and an anterior slot;
a flange, said flange shaped to be secured to a surgically prepared anterior surface of said proximal end of said patient's tibia, said flange comprising an orifice therethrough and a tab protruding therefrom, wherein when said baseplate is secured to said surgically prepared proximal end of said patients tibia, and said flange is secured to said surgically prepared anterior surface of said proximal end of said patient's tibia, said tab is inserted into said slot;
a receptacle in said first surface; and
a rod-like fastener comprising a first end, said fastener installed through said orifice, said first end of said fastener received in said receptacle.

24. The device for unicompartmental arthroplasty of claim 23, further comprising:
internal threads in said receptacle; and
external threads on said first end of said fastener, said external threads being complementary to said internal threads in said receptacle.

25. The device for unicompartmental arthroplasty of claim 23, further comprising:
at least one anchor protruding from said first surface, said at least one anchor arranged to coincide with at least one corresponding surgically prepared void in said patient's tibia.

26. The device for unicompartmental arthroplasty of claim 23, wherein said baseplate comprises a porous metal material.

27. The device for unicompartmental arthroplasty of claim 26, wherein said at least one anchor comprises a porous metal material.

28. The device for unicompartmental arthroplasty of claim 23, wherein said flange comprises a porous metal material.

29. The device for unicompartmental arthroplasty of claim 23, wherein said baseplate is configured to be secured to said patient's tibia without using cement.

30. The device for unicompartmental arthroplasty of claim 23, further comprising:
internal threads in said orifice; and
external threads on said fastener, said external threads being complementary to said internal threads in said orifice.

31. A method of performing unicompartmental arthroplasty of a patient's knee, the method comprising the steps of:
making an incision along an anterior aspect of a knee;
excising remnants of a tibial meniscus;
surgically preparing a tibia to receive a tibial prosthesis component in a manner so as to preserve any anterior and posterior cruciate ligaments found in said knee, said tibial prosthesis component having a baseplate, said baseplate comprising a first surface configured to be positioned on a surgically prepared proximal end of said tibia, and an opposing second surface configured to replicate a tibial condyle, a flange adjacent said baseplate, said flange shaped to interface with a surgically prepared anterior surface of said proximal end of said tibia, said flange comprising an orifice therethrough, and at least one anchor protruding from said first surface, said at least one anchor arranged to coincide with at least one corresponding surgically prepared void in said patient's tibia, said at least one anchor comprising a receptacle;
positioning said tibial prosthesis component on said surgically prepared proximal end of said tibia;
inserting a rod-like fastener through said orifice and into said receptacle; and
closing said incision.

32. A method of performing unicompartmental arthroplasty of a patient's knee, the method comprising the steps of:
making an incision along an anterior aspect of a knee;
excising remnants of a tibial meniscus;
surgically preparing a tibia to receive a tibial prosthesis component in a manner so as to preserve any anterior and posterior cruciate ligaments found in said knee, said tibial prosthesis component having a baseplate, said baseplate comprising a first surface comprising a receptacle, said first surface configured to be positioned on a surgically prepared proximal end of said tibia, and an opposing second surface configured to replicate a tibial condyle, a flange adjacent said baseplate, said flange shaped to interface with a surgically prepared anterior surface of said proximal end of said tibia, said flange comprising an orifice therethrough;
positioning said tibial prosthesis component on said surgically prepared proximal end of said tibia;
inserting a rod-like fastener through said orifice and into said receptacle; and
closing said incision.

* * * * *